United States Patent
Tian et al.

(10) Patent No.: US 11,816,767 B1
(45) Date of Patent: Nov. 14, 2023

(54) METHOD AND SYSTEM FOR RECONSTRUCTING MAGNETIC PARTICLE DISTRIBUTION MODEL BASED ON TIME-FREQUENCY SPECTRUM ENHANCEMENT

(71) Applicant: INSTITUTE OF AUTOMATION, CHINESE ACADEMY OF SCIENCES, Beijing (CN)

(72) Inventors: Jie Tian, Beijing (CN); Zechen Wei, Beijing (CN); Hui Hui, Beijing (CN); Xin Yang, Beijing (CN); Huiling Peng, Beijing (CN)

(73) Assignee: INSTITUTE OF AUTOMATION, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 18/218,115

(22) Filed: Jul. 5, 2023

(30) Foreign Application Priority Data

Nov. 18, 2022 (CN) .......................... 202211442910.6

(51) Int. Cl.
*G06K 9/00* (2022.01)
*G06T 11/00* (2006.01)
(Continued)

(52) U.S. Cl.
CPC .......... *G06T 11/006* (2013.01); *A61B 5/0515* (2013.01); *G06T 5/002* (2013.01);
(Continued)

(58) Field of Classification Search
CPC ......... G06T 11/006; G06T 5/002; G06T 5/10; G06T 2207/10072; G06T 2207/20081; G06T 2207/20084; A61B 5/0515
(Continued)

(56) References Cited

FOREIGN PATENT DOCUMENTS

| CN | 113628296 A | 11/2021 |
| CN | 114246574 A | 3/2022 |

OTHER PUBLICATIONS

Fang, Xiaoxin, et al. "Detection Transformer: Ultrasonic Echo Signal Inclusion Detection with Transformer." 2022 IEEE International Conference on Networking, Sensing and Control (ICNSC). IEEE, 2022. (Year: 2022).*

(Continued)

*Primary Examiner* — Jonathan S Lee
(74) *Attorney, Agent, or Firm* — Bayramoglu Law Offices LLC

(57) ABSTRACT

A method and system for reconstructing a magnetic particle distribution model based on time-frequency spectrum enhancement are provided. The method includes: scanning, by a magnetic particle imaging (MPI) device, a scan target to acquire a one-dimensional time-domain signal of the scan target; performing short-time Fourier transform to acquire a time-frequency spectrum; acquiring, by a deep neural network (DNN) fused with a self-attention mechanism, a denoised time-frequency spectrum; acquiring a high-quality magnetic particle time-domain signal; and reconstructing a magnetic particle distribution model. The method learns global and local information in the time-frequency spectrum through the DNN fused with the self-attention mechanism, thereby learning a relationship between different harmonics to distinguish between a particle signal and a noise signal. The method combines the global and local information to complete denoising of the time-frequency spectrum, thereby acquiring the high-quality magnetic particle time-domain signal.

10 Claims, 7 Drawing Sheets

(51) Int. Cl.
*G06T 5/00* (2006.01)
*G06T 5/10* (2006.01)
*A61B 5/0515* (2021.01)

(52) U.S. Cl.
CPC ...... *G06T 5/10* (2013.01); *G06T 2207/10072* (2013.01); *G06T 2207/20081* (2013.01); *G06T 2207/20084* (2013.01)

(58) Field of Classification Search
USPC ........................................................ 382/131
See application file for complete search history.

(56) References Cited

OTHER PUBLICATIONS

Wu, Xiangjun, et al. "PGNet: Projection generative network for sparse-view reconstruction of projection-based magnetic particle imaging." Medical physics 50.4 (2022): 2354-2371. (Year: 2022).*

* cited by examiner

METHOD AND SYSTEM FOR RECONSTRUCTING MAGNETIC PARTICLE DISTRIBUTION MODEL BASED ON TIME-FREQUENCY SPECTRUM ENHANCEMENT

CROSS REFERENCE TO THE RELATED APPLICATIONS

This application is based upon and claims priority to Chinese Patent Application No. 202211442910.6, filed on Nov. 18, 2022, the entire contents of which are incorporated herein by reference.

TECHNICAL FIELD

The present disclosure belongs to the field of magnetic particle imaging (MPI), and in particular relates to a method and system for reconstructing a magnetic particle distribution model based on time-frequency spectrum enhancement.

BACKGROUND

Accurately and objectively locating tumors and other lesions in clinical diagnosis and detection has always been a research hotspot and challenging issue internationally. Existing medical imaging technologies such as computed tomography (CT), magnetic resonance imaging (MRI), and single-photon emission computed tomography (SPECT) have problems such as significant harm, poor localization, and low precision. In recent years, a new, tracer-based imaging method, namely magnetic particle imaging (MPI) has been proposed. MPI can accurately locate tumors or targets by detecting the spatial concentration distribution of super-paramagnetic iron oxide nanoparticles (SPIONS) harmless to human body through tomography technology. MPI features three-dimensional (3D) imaging, high temporal-spatial resolution, and high sensitivity. It does not display anatomical structures and is not affected by background signals, so the intensity of the signal is directly proportional to the concentration of the tracer. Therefore, MPI is a new method with great potential for medical applications.

The current MPI technology is still in the development stage, and the hardware system is constantly improving and upgrading. In the MPI field, the background signal that cannot be ignored can cause artifacts in the reconstructed image, which will greatly affect the precision of the reconstructed image. The background signal mainly includes two types: harmonic interference and Gaussian noise. Some improved methods based on hardware upgrades and signal processing have been proposed for removing background noise signals. However, the method based on hardware upgrade has high requirements for the system and is difficult to operate. In the method based on signal processing, algorithms related to system matrices have a high time and calculation cost, while algorithms related to the X-space are mostly not robust enough to efficiently remove these two types of noise at the same time. Therefore, there is an urgent need in the MPI field for a method for efficiently removing different types of background noise simultaneously without increasing hardware complexity and time cost.

SUMMARY

In order to solve the above-mentioned problem that the existing MPI method cannot efficiently remove background noise such as harmonic interference and Gaussian noise simultaneously, resulting in low precision of the reconstructed model, the present disclosure provides a system for reconstructing a magnetic particle distribution model based on time-frequency spectrum enhancement. The system includes: a magnetic particle imaging (MPI) device, a scan target, and a processor, where the MPI device and the processor are connected through wired or wireless communication;

the scan target is provided within a scanning area of the MPI device; the processor is configured to control the MPI device to scan the scan target, acquire and send a one-dimensional time-domain signal of the scan target to the processor;

the processor is configured to perform short-time Fourier transform on the one-dimensional time-domain signal to acquire a two-dimensional time-frequency spectrum, denoise the two-dimensional time-frequency spectrum through a trained deep neural network (DNN) fused with a self-attention mechanism to acquire a magnetic particle time-frequency spectrum, and perform inverse Fourier transform on the magnetic particle time-frequency spectrum to acquire a high-quality magnetic particle time-domain signal;

the processor is further configured to perform model reconstruction based on the high-quality magnetic particle time-domain signal so as to acquire a high-precision model;

the DNN fused with the self-attention mechanism includes a feature extraction module, a joint denoising module, a time-frequency domain denoising module, and a feature reconstruction module;

the feature extraction module is configured to transmit an extracted primary feature map to the joint denoising module and the time-frequency domain denoising module; the joint denoising module is configured to extract a global spatial feature based on the primary feature map and acquire a jointly denoised feature map; the time-frequency domain denoising module is configured to extract local features from a time-domain dimension and a frequency-domain dimension of the primary feature map, and fuse the local features of the time-frequency spectrum into a time-frequency domain-denoised feature map; the jointly denoised feature map and the time-frequency domain-denoised feature map are connected to generate feature connection information; and the feature reconstruction module is configured to perform feature reconstruction based on the feature connection information so as to acquire a noise-free time-frequency spectrum.

Another aspect of the present disclosure provides a method for reconstructing a magnetic particle distribution model based on time-frequency spectrum enhancement, implemented based on the system for reconstructing a magnetic particle distribution model based on time-frequency spectrum enhancement, and including the following steps:

S100, scanning, by the MPI device, the scan target to acquire the one-dimensional time-domain signal of the scan target, where the scan target includes a scan phantom or biological sample;

S200, performing short-time Fourier transform on the one-dimensional time-domain signal of the scan target to acquire the two-dimensional time-frequency spectrum;

S300, acquiring, by the trained DNN fused with the self-attention mechanism, a denoised magnetic particle time-frequency spectrum based on the two-dimensional time-frequency spectrum, and performing inverse Fourier transform to acquire the high-quality magnetic particle time-domain signal; and S400, performing model reconstruction based on the high-quality magnetic particle time-domain signal to acquire the high-precision model, where the DNN fused with the self-attention mechanism includes a feature extraction module, a joint denoising module, a time-frequency domain denoising module, and a feature reconstruction module; the feature extraction module is configured to transmit an extracted primary feature map to the joint denoising module and the time-frequency domain denoising module; the joint denoising module is configured to extract a global spatial feature based on the primary feature map and acquire a jointly denoised feature map; the time-frequency domain denoising module is configured to extract local features from a time-domain dimension and a frequency-domain dimension of the primary feature map, and fuse the local features of the time-frequency spectrum into a time-frequency domain-denoised feature map; the jointly denoised feature map and the time-frequency domain-denoised feature map are connected to generate feature connection information; and the feature reconstruction module is configured to perform feature reconstruction based on the feature connection information so as to acquire a noise-free time-frequency spectrum.

In some preferred implementations, the feature extraction module specifically includes:

a feature extraction module input end, a multi-size feature analysis unit, a first feature concatenation unit, a first feature fusion convolutional layer, and a feature extraction module output end, where the multi-size feature analysis unit includes a first branch, a second branch, and a third branch that are connected in parallel by the feature extraction module input end;

the first branch includes a convolutional layer with 16 1×1 convolutional kernels;

the second branch includes two sequentially connected convolutional layers, namely a convolutional layer with 16 1×1 convolutional kernels and a convolutional layer with 32 3×3 convolutional kernels;

the third branch includes three sequentially connected convolutional layers, namely a convolutional layer with 16 1×1 convolutional kernels, a convolutional layer with 32 3×3 convolutional kernels, and a convolutional layer with 64 3×3 convolutional kernels;

an output of the first branch, an output of the second branch, and an output of the third branch are merged at an input of the first feature concatenation unit, and an output of the first feature concatenation unit is connected to the first feature fusion convolutional layer; and the feature extraction module input end is in a residual connection to the first feature fusion convolutional layer; and an input of the feature extraction module input end and an output of the first feature fusion convolutional layer are added together for output.

In some preferred implementations, the joint denoising module specifically includes:

a joint denoising module input end, a spatial attention block, a self-attention unit, a second feature fusion convolutional layer, a third feature fusion convolutional layer, and a joint denoising module output end that are sequentially connected;

the spatial attention block includes a spatial attention block input end connected to a channel average pooling layer and a channel max pooling layer; an output of the channel average pooling layer and an output of the channel max pooling layer are jointly concatenated to an input of the second feature concatenation unit; an output of the second feature concatenation unit is sequentially connected to a convolutional layer with one 3×3 convolutional kernel and a Sigmoid layer; and the joint denoising module input end is connected to the Sigmoid layer; and an input of the joint denoising module input end and an output of the Sigmoid layer are subjected to matrix multiplication for output; and the self-attention unit includes two parallel k×k self-attention blocks with different receptive fields, where k=3.5; and outputs of the two k×k self-attention blocks are added together, are then sequentially connected to the second feature fusion convolutional layer and the third feature fusion convolutional layer, and are connected to the joint denoising module output end; the second feature fusion convolutional layer is a convolutional layer with 32 3×3 convolutional kernels; and the third feature fusion convolutional layer is a convolutional layer with 16 3×3 convolutional kernels.

In some preferred implementations, the self-attention blocks each include the following components that are sequentially connected: a self-attention block input end, a first k×k convolutional layer, a first Reshape layer, a first addition unit, six self-attention layers, a second Reshape layer, a second k×k convolutional layer, a second addition unit, a third k×k convolutional layer, a first rectified linear unit (ReLU) layer, and a self-attention block output end; an output of the first Reshape layer is connected in parallel to the first addition unit and a position encoding layer; an output of the position encoding layer is connected to the first addition unit; and the self-attention block input end is in a residual connection to the second addition unit.

In some preferred implementations, the self-attention layers each include the following components that are sequentially connected: a self-attention layer input end, a multi-head attention layer, a third addition unit, a first layer-normalization layer, a feedforward network, a fourth addition unit, a second layer-normalization layer, and a self-attention layer output end; the self-attention layer input end is in a residual connection to the third addition unit; the feedforward network includes a first fully connected layer, a Gaussian error linear unit (GeLU) layer, and a second fully connected layer that are sequentially connected; the multi-head attention layer includes the following components that are sequentially connected: a multi-head attention layer input end, 8 parallel dot-product attention blocks, a feature concatenation layer, a third fully connected layer, and a multi-head attention layer output end; the dot-product attention block includes a first dot-product fully connected layer, a second dot-product fully connected layer, and a third dot-product fully connected layer that are parallel with each other; an output of the first dot-product fully connected layer and an output of the second dot-product fully connected layer are jointly connected to a matrix multiplication unit, and are sequentially connected to a normalization layer and a softmax layer; and an output of the softmax layer and the third dot-product fully connected layer are jointly connected to the matrix multiplication unit and a dot-product attention block output end.

In some preferred implementations, the time-frequency domain denoising module includes a time-frequency domain denoising module input end, a time-domain denoising branch, a frequency-domain denoising branch that are sequentially connected; the time-domain denoising branch and the frequency-domain denoising branch are parallel with each other, and are merged to form a fifth feature fusion convolutional layer and a time-frequency domain denoising module output end; and the fifth feature fusion convolutional layer is a convolutional layer with 16 1×1 convolutional kernels;

the time-domain denoising branch includes the following components that are sequentially connected: a time-domain denoising branch input end, 10 consecutive time-domain attention blocks, and a convolutional layer with 16 1×1 convolutional kernels;

the time-domain attention block includes a time-domain attention block input end, a first convolutional layer with 32 1×$k_1$ convolutional kernels, a second ReLU layer, a second convolutional layer with 32 1×$k_1$ convolutional kernels, a global average pooling layer, a Sigmoid layer, a multiplication unit, a fourth addition unit, and a time-domain attention block output end; an input of the global average pooling layer is connected to the multiplication unit; and the time-domain denoising branch input end is in a residual connection to the fourth addition unit; and the frequency-domain denoising branch is configured to replace the first convolutional layer with 32 1×$k_1$ convolutional kernels and the second convolutional layer with 32 1×$k_1$ convolutional kernels in the time-domain attention block respectively with a first convolutional layer with 32 $k_1$×1 convolutional kernels and a second convolutional layer with 32 $k_1$×1 convolutional kernels, replace the time-domain denoising branch input end and a time-domain denoising branch output end respectively with a frequency-domain denoising branch input end and a frequency-domain denoising branch output end, and remain a rest part the same as the time-domain denoising branch.

In some preferred implementations, the feature reconstruction module includes a feature reconstruction module input end, 6 consecutive groups of densely connected layer-dense addition unit, and a feature reconstruction module output end; the densely connected layers each include a densely connected layer input end connected to all dense addition units after the densely connected layers in a skip layer connection manner and sequentially connected to a sixth feature fusion convolutional layer, a seventh feature fusion convolutional layer, and the feature reconstruction module output end; the sixth feature fusion convolutional layer is a convolutional layer with 32 3×3 convolutional kernels; and the seventh feature fusion convolutional layer a convolutional layer with two 1×1 convolutional kernel; and the densely connected layers each specifically further include the following components that are sequentially connected to the densely connected layer input end: a first batch-normalization layer, a third ReLU layer, a convolutional layer with 36 1×1 convolutional kernels, a second batch-normalization layer, a fourth ReLU layer, a convolutional layer with 12 3×3 convolutional kernels, and a densely connected layer output end.

In some preferred implementations, a training method of the DNN fused with the self-attention mechanism includes:

A100, acquiring training data with a ground-truth label as to-be-processed data, where The to-be-processed data is specifically acquired as follows:

acquiring a simulated dot image, and extracting a one-dimensional time-domain signal of the simulated dot image;

superposing noise on the one-dimensional time-domain signal of the simulated dot image to acquire a noisy one-dimensional time-domain signal;

performing short-time Fourier transform on the one-dimensional time-domain signal of the simulated dot image and the noisy one-dimensional time-domain signal to acquire a simulated two-dimensional time-frequency spectrum and a noisy simulated two-dimensional time-frequency spectrum; and taking the noisy simulated two-dimensional time-frequency spectrum as the training data and the simulated two-dimensional time-frequency spectrum as the ground-truth label for the training data;

A200, inputting the to-be-processed data into the DNN fused with the self-attention mechanism;

A300, extracting, by the feature extraction module, feature maps of different sizes based on the to-be-processed data; concatenating the feature maps of different sizes; processing, by a convolutional layer, the feature maps of different sizes; and adding the feature maps of different sizes together with the to-be-processed data, so as to acquire the primary feature map;

A400, acquiring, by the joint denoising module, a channel max pooling attention feature and a channel average pooling attention feature based on the primary feature map; introducing learnable position information encoding; acquiring a global feature through multi-head attention; and acquiring the jointly denoised feature map; and acquiring, by the time-frequency domain denoising module, a time-domain feature map and a frequency-domain feature map based on the primary feature map; and adding the time-domain feature map and the frequency-domain feature map together to acquire the time-frequency domain-denoised feature map;

A500, adding the jointly denoised feature map and the time-frequency domain-denoised feature map together to form a combined feature map; and performing, by the feature reconstruction module, feature reconstruction on the combined feature map through multiple densely connected layers and convolutional layers to generate the denoised magnetic particle time-frequency spectrum;

A600, calculating, based on the denoised magnetic particle time-frequency spectrum, a training loss:

$$L_{all}=0.5*L_{real}+L_{imag}$$

where, $L_{real}$ denotes a real part error, calculated by an average absolute error; and $L_{imag}$ denotes an imaginary part error, calculated by an average square error; and A700, repeating steps A200 to A600 until the training loss is below a preset threshold or reaches a preset number of iterations, so as to acquire a trained DNN fused with the self-attention mechanism; and performing inverse Fourier transform on the generated denoised magnetic particle time-frequency spectrum to acquire the high-quality magnetic particle time-domain signal.

In some preferred implementations, the superposing noise on the one-dimensional time-domain signal of the simulated dot image to acquire a noisy one-dimensional time-domain signal specifically includes:

superposing harmonic interference and Gaussian noise on the one-dimensional time-domain signal of the simulated dot image:

$$u_n(t)=u(t)+u_G(t)+u_h(t)$$

where, u(t) denotes the one-dimensional time-domain signal of the simulated dot image; $u_G(t)$ denotes the Gaussian noise; $u_h(t)$ denotes the harmonic interference; and $u_n(t)$ denotes the noisy one-dimensional time-domain signal;

$$u_h(t) = \sum_{n=1}^{6} A_n \sin(2\pi f_n t + \theta_n)$$

n denotes an n-th harmonic; $f_n$ denotes a harmonic frequency; $\theta_n$ denotes a random phase that is uniformly distributed in $[0,2\pi]$; and $A_n$ denotes amplitude of an additional harmonic;

the amplitude of the additional harmonic is calculated according to a signal interference ratio equation:

$$SIR = 20\log_{10}\left(\frac{\max_{f_n}|U_n(f_n)|}{A_n}\right)$$

where, SIR denotes a set noise level; and $U_n(*)$ denotes a bandwidth of the n-th harmonic of the one-dimensional time-domain signal of the simulated dot image;

the Gaussian noise $u_G(t)$ is calculated as follows:

$$SNR = 20\log_{10}\left(\frac{\max_{t}|u(t)|}{\sigma}\right)$$

where, SNR denotes a signal-to-noise ratio; a denotes a standard deviation of noise; and u(t) denotes the one-dimensional time-domain signal of the simulated dot image.

The present disclosure has the following advantages:

The present disclosure combines the time-domain and frequency-domain to form the two-dimensional time-frequency spectrum, which includes more information than a simple one-dimensional signal. The present disclosure learns global information in the two-dimensional time-frequency spectrum and local information in the time-domain dimension and the frequency-domain dimension through the DNN fused with the self-attention mechanism, thereby learning the relationship between different harmonics to distinguish the particle signal and the background noise. The present disclosure further extracts the particle and noise information by fusing the local and global information, and completes denoising of the time-frequency spectrum, thereby acquiring the high-quality magnetic particle time-domain signal. The present disclosure achieves the simultaneous removal of multiple types of noise without increasing hardware complexity and time cost. The present disclosure can reconstruct high-precision lesion area models from the high-quality signal acquired. The present disclosure realizes the high application value of the MPI technology in the medical field and promotes the application of the MPI reconstruction technology in two-dimensional time-frequency spectrums. Compared to the one-dimensional signal technology, the present disclosure can utilize more information in the two-dimensional time-frequency spectrum to achieve higher-accuracy reconstruction.

BRIEF DESCRIPTION OF THE DRAWINGS

Other features, objectives and advantages of the present disclosure will become more apparent upon reading the detailed description of the non-restrictive embodiments with reference to the following drawings.

DETAILED DESCRIPTION OF THE EMBODIMENTS

Figure 1:
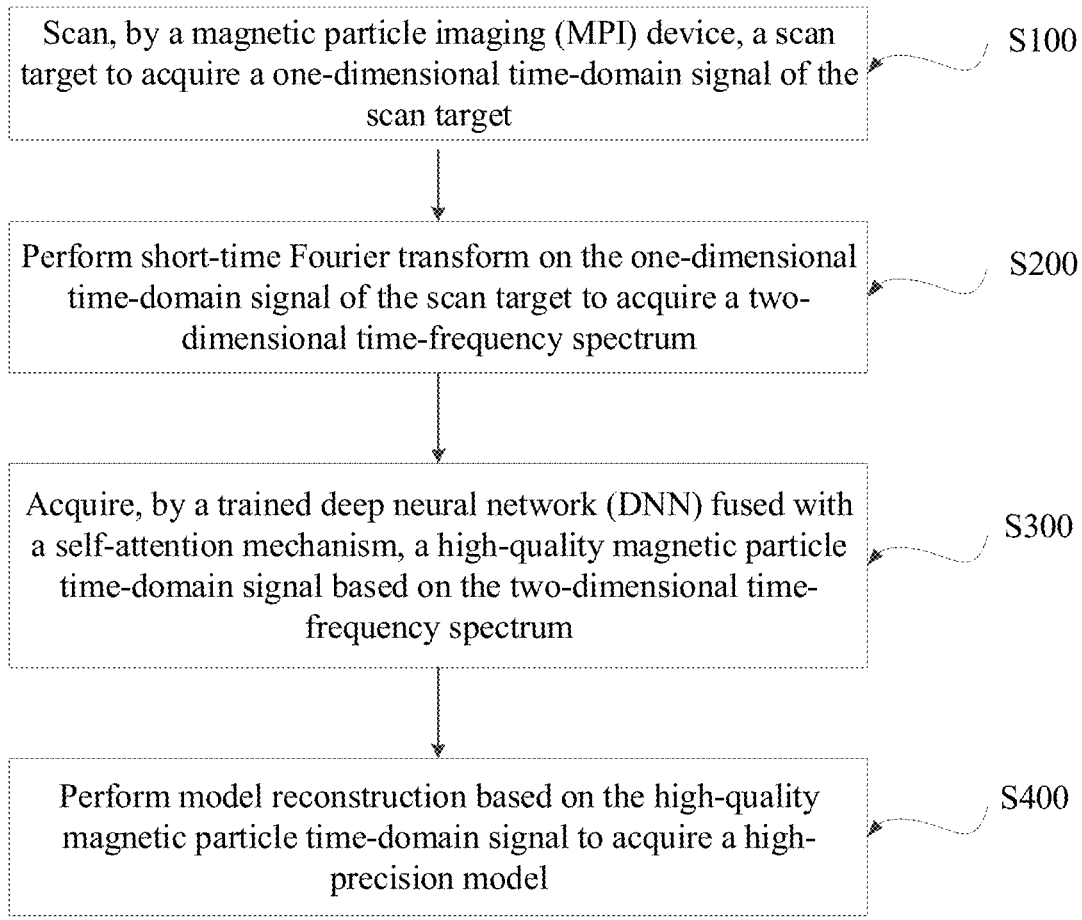
FIG. 1 is a flowchart of a method for reconstructing a magnetic particle distribution model based on time-frequency spectrum enhancement according to an embodiment of the present disclosure.

The present disclosure will be further described in detail below in conjunction with the drawings and embodiments. It should be understood that the specific embodiments described herein are merely intended to explain the present disclosure, rather than to limit the present disclosure. It should also be noted that, for convenience of description, only the parts related to the present disclosure are shown in the drawings.

It should be noted that the examples in the disclosure and features in the examples may be combined with each other in a non-conflicting situation. The present disclosure will be described in detail below with reference to the drawings and embodiments.

The present disclosure provides a system for reconstructing a magnetic particle distribution model based on time-frequency spectrum enhancement. This system learns global information in a time-frequency spectrum through a DNN fused with a self-attention mechanism, thereby learning a relationship between different harmonics to distinguish between a particle signal and a noise signal. This system further extracts the particle and noise information, and combines local and global information to complete denoising of the time-frequency spectrum, thereby acquiring a high-quality magnetic particle time-domain signal. In this way, this system reconstructs a high-precision lesion area model.

The system for reconstructing a magnetic particle distribution model based on time-frequency spectrum enhancement includes: a magnetic particle imaging (MPI) device, a scan target, and a processor.

The MPI device and the processor are connected through wired or wireless communication.

The scan target is provided within a scanning area of the MPI device; the processor is configured to control the MPI device to scan the scan target, acquire and send a one-dimensional time-domain signal of the scan target to the processor.

The processor is configured to perform short-time Fourier transform on the one-dimensional time-domain signal to acquire a two-dimensional time-frequency spectrum, denoise the two-dimensional time-frequency spectrum through a trained deep neural network (DNN) fused with a self-attention mechanism to acquire a magnetic particle time-frequency spectrum, and perform inverse Fourier transform on the magnetic particle time-frequency spectrum to acquire a high-quality magnetic particle time-domain signal.

The processor is further configured to perform model reconstruction based on the high-quality magnetic particle time-domain signal so as to acquire a high-precision model.

The DNN fused with the self-attention mechanism includes a feature extraction module, a joint denoising module, a time-frequency domain denoising module, and a feature reconstruction module.

The feature extraction module is configured to transmit an extracted primary feature map to the joint denoising module and the time-frequency domain denoising module. The joint denoising module is configured to extract a global spatial feature based on the primary feature map and acquire a jointly denoised feature map. The time-frequency domain denoising module is configured to extract local features from a time-domain dimension and a frequency-domain dimension of the primary feature map, and fuse the local features of the time-frequency spectrum into a time-frequency domain-denoised feature map. The jointly denoised feature map and the time-frequency domain-denoised feature map are connected to generate feature connection information. The feature reconstruction module is configured to perform feature reconstruction based on the feature connection information so as to acquire a noise-free time-frequency spectrum.

To more clearly explain a method for reconstructing a magnetic particle distribution model based on time-frequency spectrum enhancement provided by the present disclosure, steps in the embodiments of the present disclosure are described in detail below according to FIG. 1.

A second embodiment of the present disclosure provides a method for reconstructing a magnetic particle distribution model based on time-frequency spectrum enhancement. The method includes steps S100 to S400, which are described in detail below.

S100. The scan target is scanned by the MPI device to acquire the one-dimensional time-domain signal of the scan target, where the scan target includes a scan phantom or biological sample.

S200. Short-time Fourier transform is performed on the one-dimensional time-domain signal to acquire the two-dimensional time-frequency spectrum. In this embodiment, the time-domain signal is first divided into frames of equal length, and the short-time Fourier transform is performed on each frame. The division of each frame is based on the number of time-domain signal points corresponding to three excitation periods.

S300. A denoised magnetic particle time-frequency spectrum is acquired by the trained DNN fused with the self-attention mechanism based on the two-dimensional time-frequency spectrum, and inverse Fourier transform is performed to acquire the high-quality magnetic particle time-domain signal.

S400. Model reconstruction is performed based on the high-quality magnetic particle time-domain signal to acquire the high-precision model. Based on the high-quality magnetic particle time-frequency spectrum, the real and imaginary parts are restored to complex form, and the time-frequency spectrum is supplemented back to its original size through zero filling operation. The high-quality one-dimensional time-domain signal is acquired through inverse Fourier transform, thereby acquiring the corresponding reconstructed image result.

Figure 2:
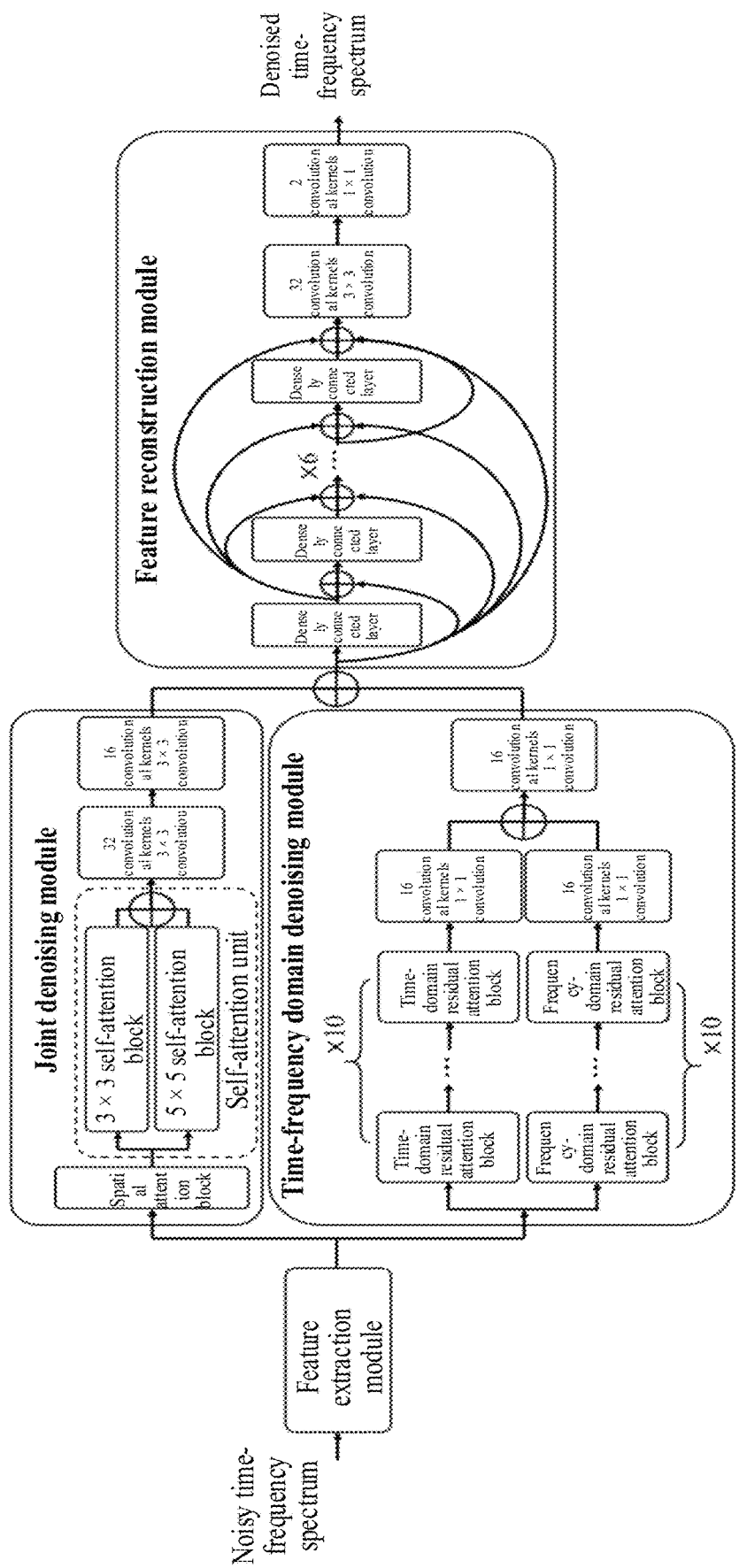
FIG. 2 is an overall structural diagram of a deep neural network (DNN) fused with a self-attention mechanism according to an embodiment of the present disclosure.

As shown in FIG. 2, the DNN fused with the self-attention mechanism includes a feature extraction module, a joint denoising module, a time-frequency domain denoising module, and a feature reconstruction module. The feature extraction module is configured to extract and transmit an extracted primary feature map to the joint denoising module and the time-frequency domain denoising module. The joint denoising module is configured to extract a global spatial feature based on the primary feature map and acquire a jointly denoised feature map. The time-frequency domain denoising module is configured to extract local features from a time-domain dimension and a frequency-domain dimension of the primary feature map, and fuse the local features of the time-frequency spectrum into a time-frequency domain-denoised feature map. The jointly denoised feature map and the time-frequency domain-denoised feature map are connected to generate feature connection information. The feature reconstruction module is configured to perform feature reconstruction based on the feature connection information so as to acquire a noise-free time-frequency spectrum.

In the present disclosure, the processing object of the DNN fused with the self-attention mechanism is the time-frequency spectrum, which is two-dimensional data and essentially a signal. The width of the spectrum denotes the time information, specifically the magnetic particle scanning track and particle concentration distribution information of each frame of the short-time Fourier transform. Specifically, if there are particles in the frame of time or track, the corresponding time-frequency spectrum has a large amplitude. The height of the spectrum denotes the frequency-domain information, specifically different multiple and non-multiple harmonics information of the signal. There is a nonlinear mathematical relationship between these harmonics, which includes information that decreases from low to high frequencies, meaning that low frequencies include more information. Therefore, the two-dimensional time-frequency spectrum is treated as an image for processing. In addition, because the time-frequency spectrum is complex, the real and imaginary parts are taken out separately as two channels. Therefore, the input is $H \times W \times 2$, where H and W denote the height and width of the time-frequency spectrum, respectively. Optionally, H takes 6, and W takes 21. In addition, 2 denotes the two channels, namely the real part and the imaginary part.

The existing methods are based on a single dimension, namely the time-domain (X-space) or frequency-domain (system matrix) of the signal for processing. The present disclosure combines the time-domain information and the frequency-domain information to form the time-frequency spectrum for processing.

The existing two types of methods (based on X-space or system matrix) cannot simultaneously process the time-domain data and frequency-domain data, so they cannot achieve reconstruction based on the time-frequency spectrum. In the present disclosure, the neural network model avoids this problem by considering the real and imaginary parts as two input channels to simultaneously process the time-domain information and the frequency-domain information.

Figure 3:
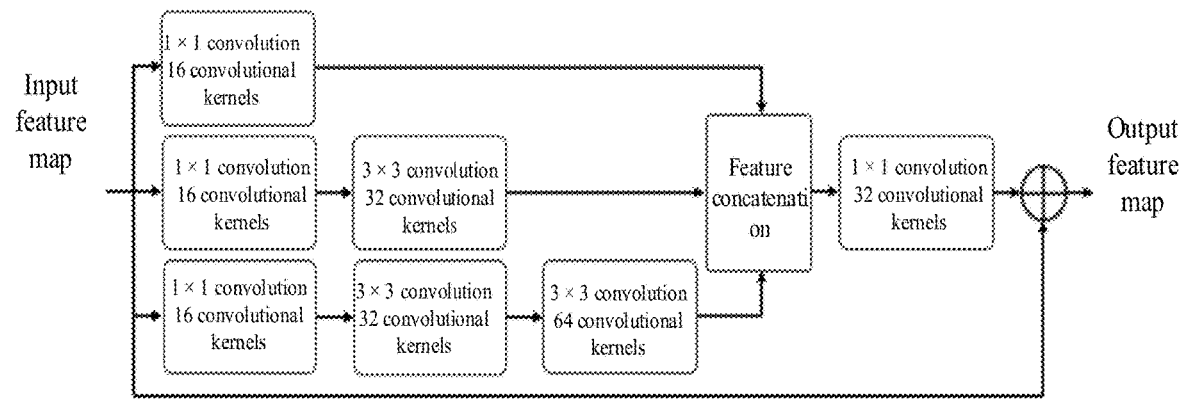
FIG. 3 is a structural diagram of a feature extraction module according to an embodiment of the present disclosure.

In this embodiment, as shown in FIG. 3, the feature extraction module specifically includes:

a feature extraction module input end, a multi-size feature analysis unit, a first feature concatenation unit, a first feature fusion convolutional layer, and a feature extraction module output end, where the first feature fusion convolutional layer is a convolutional layer with 32 1×1 convolutional kernels.

The multi-size feature analysis unit includes a first branch, a second branch, and a third branch that are connected in parallel by the feature extraction module input end.

The first branch includes a convolutional layer with 16 1×1 convolutional kernels.

The second branch includes two sequentially connected convolutional layers, namely a convolutional layer with 16 1×1 convolutional kernels and a convolutional layer with 32 3×3 convolutional kernels.

The third branch includes three sequentially connected convolutional layers, namely a convolutional layer with 16 1×1 convolutional kernels, a convolutional layer with 32 3×3 convolutional kernels, and a convolutional layer with 64 3×3 convolutional kernels.

An output of the first branch, an output of the second branch, and an output of the third branch are merged at an input of the first feature concatenation unit, and an output of the first feature concatenation unit is connected to the first feature fusion convolutional layer, where the first feature fusion convolutional layer is a convolutional layer with 32 1×1 convolutional kernels.

The feature extraction module input end is in a residual connection to the first feature fusion convolutional layer; and an input of the feature extraction module input end and an output of the first feature fusion convolutional layer are added together for output. The (H×W×32) feature map finally output by the feature extraction module is taken as an input of the joint denoising module and the time-frequency domain denoising module.

The main function of the feature extraction module is to extract the feature of the time-frequency spectrum. As previously mentioned, the time-frequency spectrum is treated as an image for processing, so it is necessary to expand its feature channels for subsequent learning. In this embodiment, three branches represent three sizes, namely receptive fields 1×1, 3×3 and 5×5, for feature extraction. The third branch uses two 3×3 instead of 5×5. Because the input takes the first six harmonics of the time-frequency spectrum, the height of the time-frequency spectrum is 6, and 5×5 is the maximum size (7×7 is larger than the input size, and even-size convolutional kernels are generally not used). In terms of the time-frequency spectrum, 5 in the frequency-domain denotes five consecutive harmonics. The connection between higher harmonics is not so strong, so it is not necessary to extract features. 5 in the time-domain denotes five consecutive time periods. Similarly, from the scanning track, the connections are insufficient within a larger range to extract more features. Therefore, convolutional kernels at sizes 1, 3, and 5 are selected to extract features. In addition, the number of convolutional kernels in each convolutional layer is an empirical parameter, which is a compromise between the total number of model parameters and model performance.

In this embodiment, the joint denoising module specifically includes: a joint denoising module input end, a spatial attention block, a self-attention unit, a second feature fusion convolutional layer, a third feature fusion convolutional layer, and a joint denoising module output end that are sequentially connected.

Figure 4:
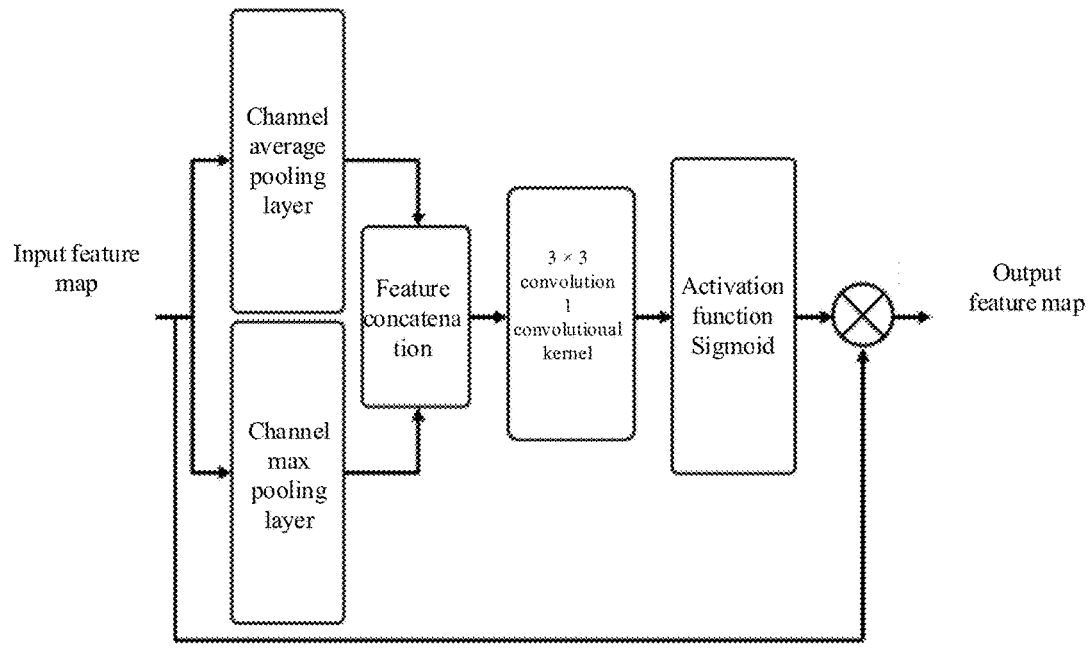
FIG. 4 is a structural diagram of a spatial attention block according to an embodiment of the present disclosure.

As shown in FIG. 4, the spatial attention block includes a spatial attention block input end connected to a channel average pooling layer and a channel max pooling layer. An output of the channel average pooling layer and an output of the channel max pooling layer are jointly concatenated to an input of the second feature concatenation unit. An output of the second feature concatenation unit is sequentially connected to a convolutional layer with one 3×3 convolutional kernel and a Sigmoid layer. The joint denoising module input end is connected to the Sigmoid layer. An input of the joint denoising module input end and an output of the Sigmoid layer are subjected to matrix multiplication for output. The channel average pooling layer and the channel max pooling layer can acquire different attention features. By concatenating two different attention features and multiplying the attention features obtained through convolution and Sigmoid functions with the original input of the spatial attention block, the output of the spatial attention block is obtained as the input of the self-attention block.

The self-attention unit includes two parallel k×k self-attention blocks with different receptive fields, where k=3.5. Outputs of the two k×k self-attention blocks are added together, are then sequentially connected to the second feature fusion convolutional layer and the third feature fusion convolutional layer, and are connected to the joint denoising module output end. In this embodiment, the second feature fusion convolutional layer is a convolutional layer with 32 3×3 convolutional kernels; and the third feature fusion convolutional layer is a convolutional layer with 16 3×3 convolutional kernels.

Figure 5:
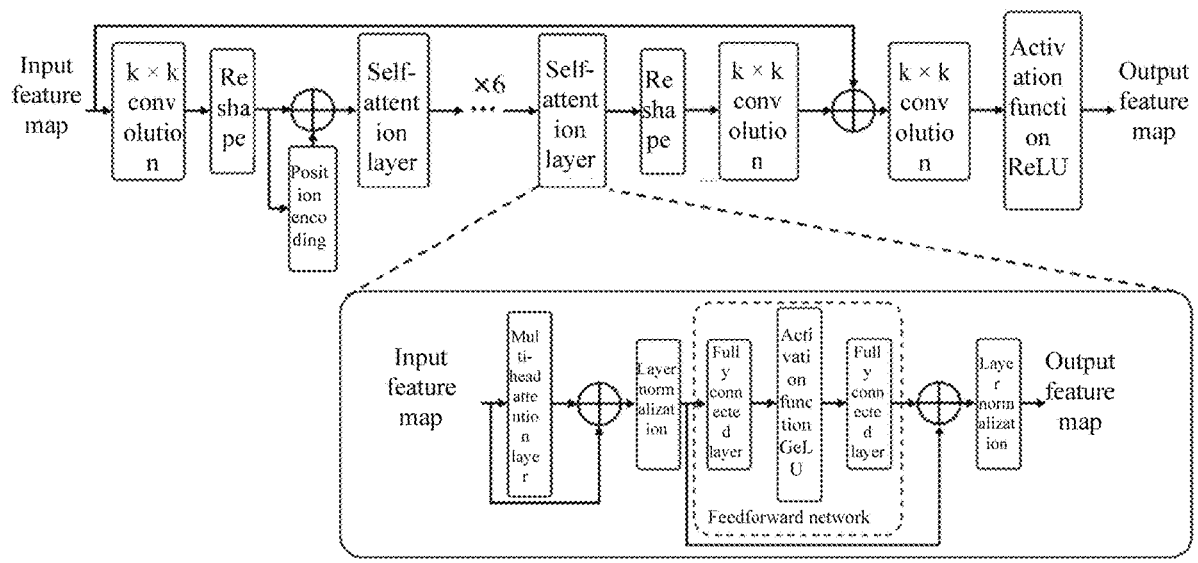
FIG. 5 is a structural diagram of a self-attention block according to an embodiment of the present disclosure.

In this embodiment, as shown in FIG. 5, the self-attention blocks each include the following components that are sequentially connected: a self-attention block input end, a first k×k convolutional layer, a first Reshape layer, a first addition unit, six self-attention layers, a second Reshape layer, a second k×k convolutional layer, a second addition unit, a third k×k convolutional layer, a first rectified linear unit (ReLU) layer, and a self-attention block output end. An output of the first Reshape layer is connected in parallel to the first addition unit and a position encoding layer. An output of the position encoding layer is connected to the first addition unit. The self-attention block input end is in a residual connection to the second addition unit. In the self-attention block, the feature map is reshaped into a two-dimensional (H×W)×32 input into the self-attention layer through the first reshape layer. Meanwhile, learnable position encoding is introduced and directly added to fuse with the feature map, so as to encode the position information of the feature input into the self-attention layer. The feature map is input into the 6 consecutive self-attention layers. Each self-attention layer includes a multi-head self-attention layer and a feedforward network. The output of the self-attention layer is reshaped into a three-dimensional (H×W×32) feature map through the second reshape layer. The outputs of the two self-attention blocks are connected through the feature map, and two 3×3 convolution operations are performed to acquire the output of the joint denoising module. The feedforward network includes a fully connected layer, a GeLU layer, and a fully connected layer that are sequentially connected.

Figure 6:
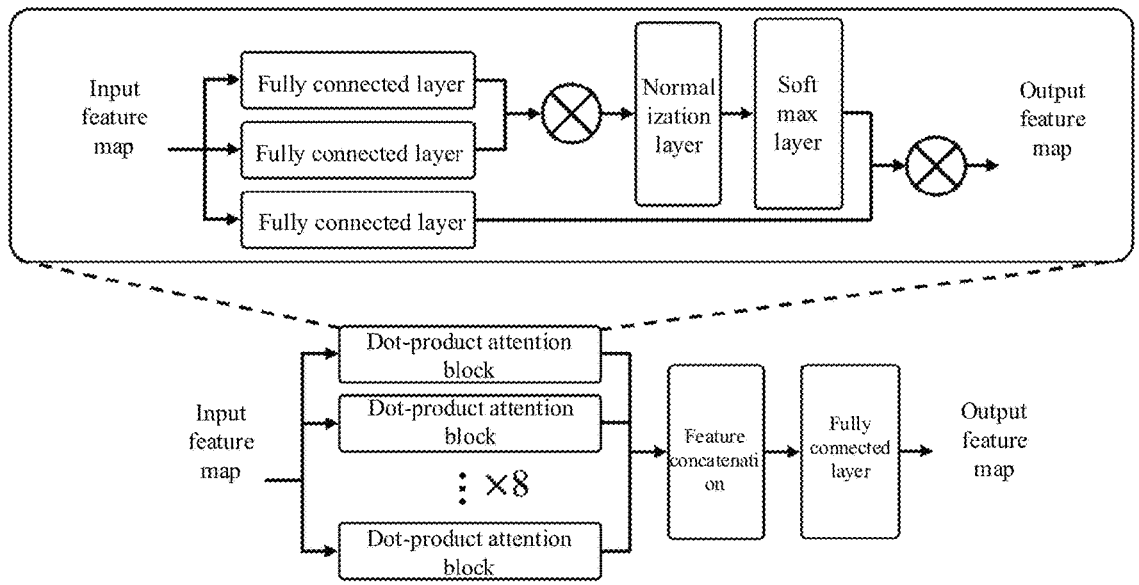
FIG. 6 is a structural diagram of a multi-head attention layer according to an embodiment of the present disclosure.

In this embodiment, the self-attention layers each include the following components that are sequentially connected: a self-attention layer input end, a multi-head attention layer, a third addition unit, a first layer-normalization layer, a feedforward network, a fourth addition unit, a second layer-normalization layer, and a self-attention layer output end. The self-attention layer input end is in a residual connection to the third addition unit. The feedforward network includes a first fully connected layer, a Gaussian error linear unit (GeLU) layer, and a second fully connected layer that are sequentially connected. As shown in FIG. 6, the multi-head attention layer includes the following components that are sequentially connected: a multi-head attention layer input end, 8 parallel dot-product attention blocks, a feature concatenation layer, a third fully connected layer, and a multi-head attention layer output end. The input feature map is first processed through the parallel 8 dot-product attention blocks to acquire the corresponding feature vectors. Then, 8 feature vectors undergo feature concatenations and are processed through the fully connected layer to acquire a feature map output by the global attention mechanism. The dot-product attention block includes a first dot-product fully connected layer, a second dot-product fully connected layer, and a third dot-product fully connected layer that are parallel with each other. An output of the first dot-product fully connected layer and an output of the second dot-product fully connected layer are jointly connected to a matrix multiplication unit, and are sequentially connected to a normalization layer and a softmax layer. An output of the softmax layer and the third dot-product fully connected layer are jointly connected to the matrix multiplication unit and a dot-product attention block output end.

The main purpose of the joint denoising module is to extract a global feature and remove the noise from a global perspective. The main function of the spatial attention block is to make the network focus on a part with a larger feature map value, i.e. a part with a greater noise impact. In the attention unit, the two parallel attention blocks have the same structure to extract the global feature for denoising. Similar to the feature extraction module, the selection of the sizes 3 and 5 mainly considers the size of the time-frequency spectrum (H=6). Considering that the goal is to extract the global features, it is not necessary to process individual pixel points (i.e. to use convolutional kernels of size 1). This module only selects kernels of sizes 3 and 5. After the features are output from the self-attention unit, they are fused through two convolutional layers.

In this embodiment, the time-frequency domain denoising module includes a time-frequency domain denoising module input end, a time-domain denoising branch, a frequency-domain denoising branch that are sequentially connected. The time-domain denoising branch and the frequency-domain denoising branch are parallel with each other, and are merged to form a fifth feature fusion convolutional layer and a time-frequency domain denoising module output end.

The time-domain denoising branch includes the following components that are sequentially connected: a time-domain denoising branch input end, 10 consecutive time-domain attention blocks, and a convolutional layer with 16 1×1 convolutional kernels.

Figure 7:
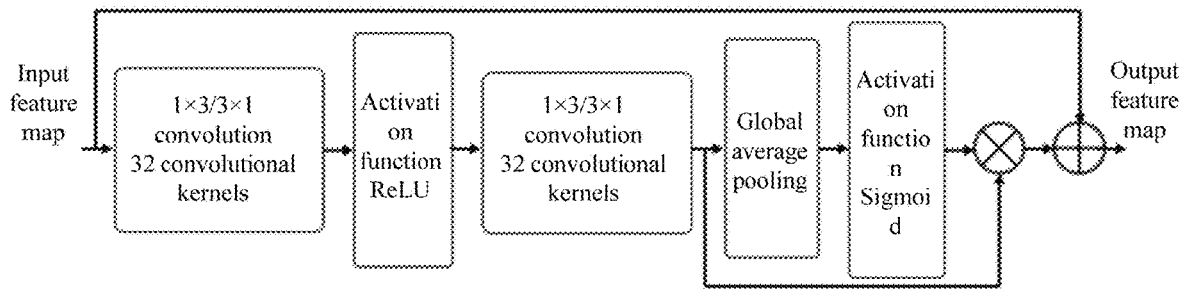
FIG. 7 is a structural diagram of a time-domain residual attention block and frequency-domain residual attention block according to an embodiment of the present disclosure.
Figure 8:
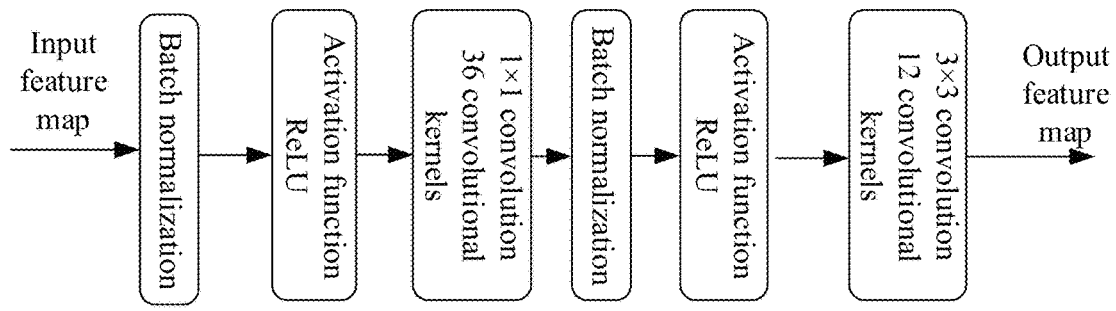
FIG. 8 is a structural diagram of a densely connected layer according to an embodiment of the present disclosure.

As shown in FIG. 7, the time-domain attention block includes a time-domain attention block input end, a first convolutional layer with 32 1×$k_1$ convolutional kernels, a second ReLU layer, a second convolutional layer with 32 1×$k_1$ convolutional kernels, a global average pooling layer, a Sigmoid layer, a multiplication unit, a fourth addition unit, and a time-domain attention block output end. An input of the global average pooling layer is connected to the multiplication unit. The time-domain denoising branch input end is in a residual connection to the fourth addition unit.

The frequency-domain denoising branch is configured to replace the first convolutional layer with 32 1×$k_1$ convolutional kernels and the second convolutional layer with 32 1×$k_1$ convolutional kernels in the time-domain attention block respectively with a first convolutional layer with 32 $k_1$×1 convolutional kernels and a second convolutional layer with 32 $k_1$×1 convolutional kernels, replace the time-domain denoising branch input end and a time-domain denoising branch output end respectively with a frequency-domain denoising branch input end and a frequency-domain denoising branch output end, and remain a rest part the same as the time-domain denoising branch.

In this embodiment, the purpose of the time-frequency domain denoising module is to extract local features from the time-domain dimension and the frequency-domain dimension for denoising. The consecutive time/frequency domain residual attention blocks are used to extract local features. The number (10) of the consecutive time/frequency domain residual attention blocks is an empirical parameter that balances the total number of model parameters and model performance. The features output by the two branches are connected and fused through the convolutional layers.

In this embodiment, the feature reconstruction module includes a feature reconstruction module input end, 6 consecutive groups of densely connected layer-dense addition unit, and a feature reconstruction module output end. As shown in FIG. 2, the densely connected layers each include a densely connected layer input end connected to all dense addition units after the densely connected layers in a skip layer connection manner and sequentially connected to a sixth feature fusion convolutional layer, a seventh feature fusion convolutional layer, and the feature reconstruction module output end. The sixth feature fusion convolutional layer is a convolutional layer with 32 3×3 convolutional kernels; and the seventh feature fusion convolutional layer a convolutional layer with two 1×1 convolutional kernel.

The features output by the joint denoising module and the time-frequency domain denoising module are added and input into the feature reconstruction module. The purpose of the feature reconstruction module is to fuse the denoised global and local features, in order to acquire a noise-free time-frequency spectrum. For the densely connected layers, structurally, the feature map output by each block is the input of all subsequent blocks, achieved through skip layer connections. This structure strengthens the transfer of features, effectively utilizes features, facilitates feature fusion, and acquires the final noise-free time-frequency spectrum. Here, the consecutive number is 6, which is also an empirical parameter.

The densely connected layers each specifically further include the following components that are sequentially connected to the densely connected layer input end: a first batch-normalization layer, a third ReLU layer, a convolutional layer with 36 1×1 convolutional kernels, a second batch-normalization layer, a fourth ReLU layer, a convolutional layer with 12 3×3 convolutional kernels, and a densely connected layer output end.

Figure 9:
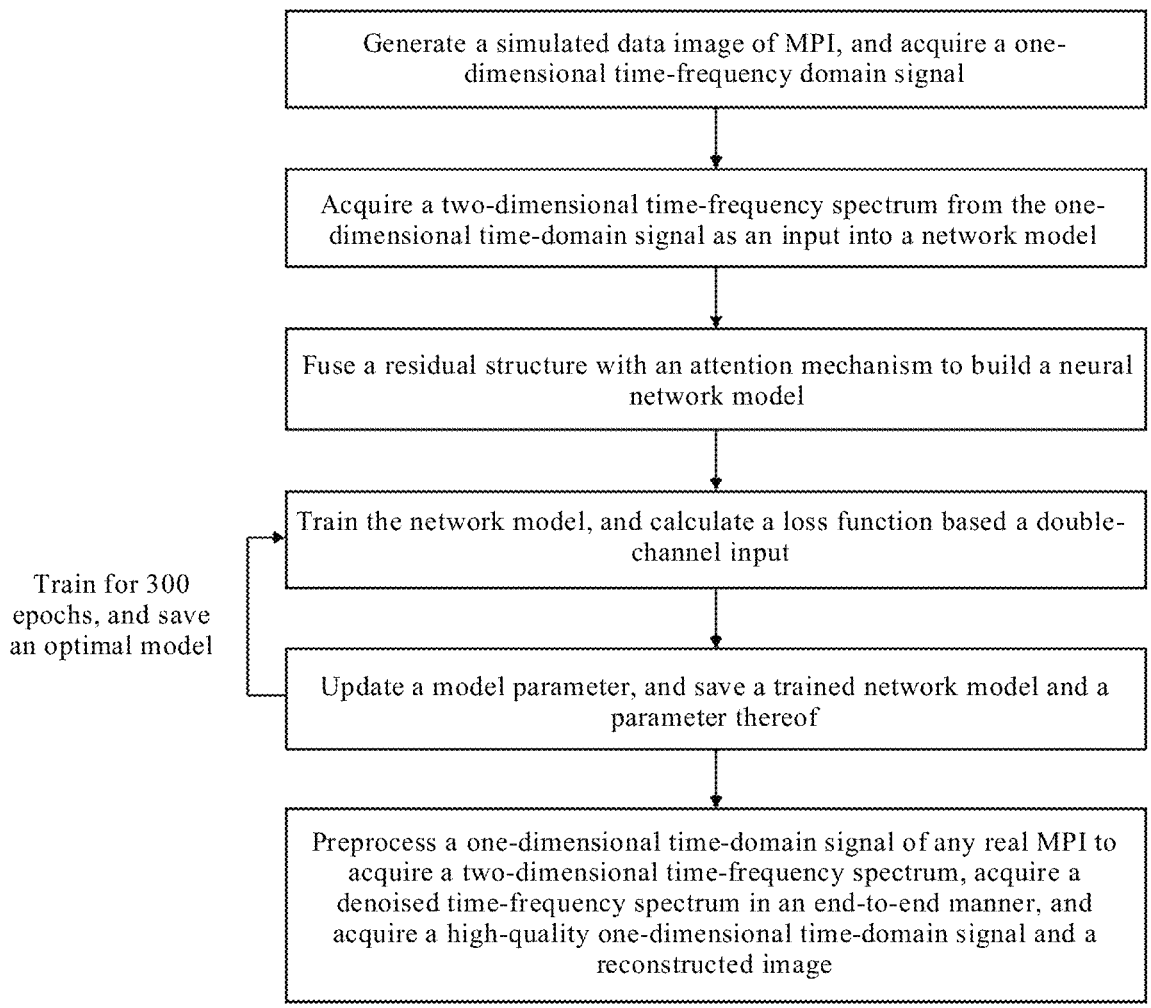
FIG. 9 is an overall flowchart of a process from data acquisition to actual detection according to an embodiment of the present disclosure.
Figure 10:
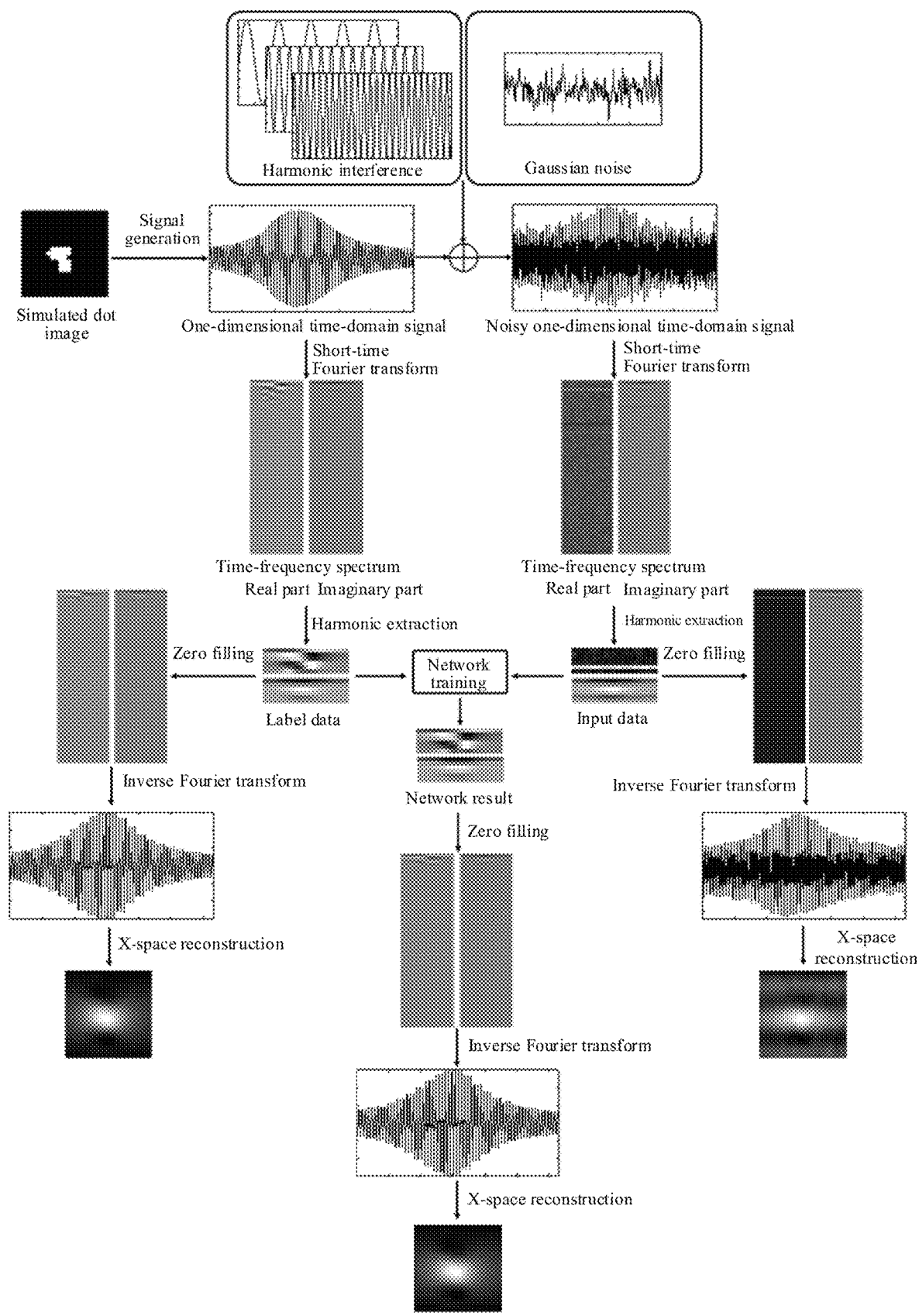
FIG. 10 is a schematic diagram of the process from data acquisition to network training (without actual detection) according to an embodiment of the present disclosure.

In this embodiment, a training method of the DNN fused with the self-attention mechanism includes:

A100. Training data with a ground-truth label is acquired as to-be-processed data. As shown in FIGS. 9 and 10, the process of the present disclosure from the acquisition of the training data to practical application is described below.

In this embodiment, the to-be-processed data is specifically acquired as follows.

A simulated dot image is acquired, and a one-dimensional time-domain signal of the simulated dot image is extracted.

Noise is superposed on the one-dimensional time-domain signal of the simulated dot image to acquire a noisy one-dimensional time-domain signal.

Short-time Fourier transform is performed on the one-dimensional time-domain signal of the simulated dot image and the noisy one-dimensional time-domain signal to acquire a simulated two-dimensional time-frequency spectrum and a noisy simulated two-dimensional time-frequency spectrum.

The noisy simulated two-dimensional time-frequency spectrum is taken as the training data, and the simulated two-dimensional time-frequency spectrum is taken as the ground-truth label for the training data;

In this embodiment, the noise is superposed on the one-dimensional time-domain signal of the simulated dot image to acquire a noisy one-dimensional time-domain signal. This step specifically includes:

Harmonic interference and Gaussian noise are superposed on the one-dimensional time-domain signal of the simulated dot image:

$$u_n(t)=u(t)+u_G(t)+u_h(t)$$

where, $u(t)$ denotes the one-dimensional time-domain signal of the simulated dot image; $u_G(t)$ denotes the Gaussian noise; $u_h(t)$ denotes the harmonic interference; and $u_n(t)$ denotes the noisy one-dimensional time-domain signal.

$$u_h(t) = \sum_{n=1}^{6} A_n \sin(2\pi f_n t + \theta_n)$$

n denotes an n-th harmonic; $f_n$ denotes a harmonic frequency; $\theta_n$ denotes a random phase that is uniformly distributed in $[0,2\pi]$; and $A_n$ denotes amplitude of an additional harmonic. In this embodiment, only the first six harmonics are taken.

The amplitude of the additional harmonic is calculated according to a signal interference ratio equation:

$$SIR = 20\log_{10}\left(\frac{\max_{f_n}|U_n(f_n)|}{A_n}\right)$$

where, SIR denotes a set noise level; and $U_n(*)$ denotes a bandwidth of the n-th harmonic of the one-dimensional time-domain signal of the simulated dot image.

The Gaussian noise $u_G(t)$ is calculated as follows:

$$SNR = 20\log_{10}\left(\frac{\max_{t}|u(t)|}{\sigma}\right)$$

where, SNR denotes a signal-to-noise ratio; $\sigma$ denotes a standard deviation of noise; and $u(t)$ denotes the one-dimensional time-domain signal of the simulated dot image.

In this embodiment, 100,000 simulated dot images (21×21) are used to simulate MPI in a real situation. The simulated dot images are grayscale images with a grayscale value distribution of 0-255. The size, position, grayscale value (simulating different concentrations), and number (2-5) of dots in the simulated image are randomly distributed to simulate the result of MPI in the real situation. The simulated image simulates the distribution of magnetic particles in the real situation, and acquires a corresponding one-dimensional time-domain signal (1×12,600) through a simulated scanning process.

In Step S200, the acquired two-dimensional time-frequency spectrum is a two-dimensional array, with each column being complex to represent the frequency-domain information corresponding to different time periods. In frequency-domain extraction, only the first six harmonics are taken. The real and imaginary parts of the processed time-frequency spectrum (6×21) are taken out separately to acquire input data and label data of 6×21×2. A total of 100,000 sets of noisy time-frequency spectrum as input data and noise-free time-frequency spectrum as label data are acquired as a training dataset for the neural network.

A200. The to-be-processed data is input into the DNN fused with the self-attention mechanism.

A300. Feature maps of different sizes are extracted by the feature extraction module based on the to-be-processed data; concatenating the feature maps of different sizes. The feature maps of different sizes are processed by a convolutional layer. The feature maps of different sizes are added together with the to-be-processed data, so as to acquire the primary feature map.

A400. A channel max pooling attention feature and a channel average pooling attention feature are acquired by the joint denoising module based on the primary feature map. Learnable position information encoding is introduced. A global feature is acquired through multi-head attention, and the jointly denoised feature map is acquired.

A time-domain feature map and a frequency-domain feature map are acquired by the time-frequency domain denoising module based on the primary feature map. The time-domain feature map and the frequency-domain feature map are added together to acquire the time-frequency domain-denoised feature map.

A500. The jointly denoised feature map and the time-frequency domain-denoised feature map are added together to form a combined feature map. Feature reconstruction is performed by the feature reconstruction module on the combined feature map through multiple densely connected layers and convolutional layers to generate the denoised magnetic particle time-frequency spectrum.

A600. Based on the denoised magnetic particle time-frequency spectrum, a training loss is calculated as follows:

$$L_{all}=0.5 *L_{real}+L_{imag}$$

where, $L_{real}$ denotes a real part error, calculated by an average absolute error; and $L_{imag}$ denotes an imaginary part error, calculated by an average square error. The output result 6×21×2 is divided into real part 6×21×1 and imaginary part 6×21×1, and the error between the real part as well as the imaginary part and the label is calculated.

A700. Steps A200 to A600 are repeated until the training loss is below a preset threshold or reaches a preset number of iterations, so as to acquire a trained DNN fused with the self-attention mechanism. Inverse Fourier transform is performed on the generated denoised magnetic particle time-frequency spectrum to acquire the high-quality magnetic particle time-domain signal. In this embodiment, the training is performed for 300 epochs.

These steps are described in order in the above embodiments. However, those skilled in the art may understand that, in order to achieve the effects of these embodiments, different steps may not be necessarily executed in such an order, but may be executed simultaneously (in parallel) or in a reversed order. These simple changes should fall within the protection scope of the present disclosure.

Those skilled in the art should be aware that the modules and method steps of the examples described in the embodiments disclosed herein may be implemented by electronic hardware, computer software or a combination thereof. The programs corresponding to software modules and method steps may be placed in random access memory (RAM), internal memory, read-only memory (ROM), electrically programmable ROM, electrically erasable programmable ROM, registers, hard disk, removable disk, compact disc read-only memory (CD-ROM), or in any other form of storage medium known in the technical field. In order to clearly illustrate the interchangeability of the electronic hardware and software, the composition and steps of each example are generally described in accordance with the function in the above description. Whether the functions are performed by electronic hardware or software depends on particular applications and design constraints of the technical solutions. Those skilled in the art may use different methods to implement the described functions for each specific application, but such implementation should not be considered to be beyond the scope of the present disclosure.

Terms such as "first" and "second" are intended to distinguish between similar objects, rather than describe or indicate a specific order or sequence.

Terms "include", "comprise" or any other variations thereof are intended to cover non-exclusive inclusions, so that a process, a method, an article, or a device/apparatus including a series of elements not only includes those elements, but also includes other elements that are not explicitly listed, or also includes inherent elements of the process, the method, the article or the device/apparatus.

The technical solutions of the present disclosure are described with reference to the preferred implementations and drawings. Those skilled in the art should easily understand that the protection scope of the present disclosure is apparently not limited to these specific implementations. Those skilled in the art can make equivalent changes or substitutions to the relevant technical features without departing from the principles of the present disclosure, and the technical solutions after these changes or substitutions should fall within the protection scope of the present disclosure.

What is claimed is:

1. A method for reconstructing a magnetic particle distribution model based on a time-frequency spectrum enhancement, comprising the following steps:
    S100, scanning, by a magnetic particle imaging (MPI) device, a scan target to acquire a one-dimensional time-domain signal of the scan target;
    S200, performing short-time Fourier transform on the one-dimensional time-domain signal of the scan target to acquire a two-dimensional time-frequency spectrum;
    S300, acquiring, by a trained deep neural network (DNN) fused with a self-attention mechanism, a denoised magnetic particle time-frequency spectrum based on the two-dimensional time-frequency spectrum, and performing inverse Fourier transform to acquire a high-quality magnetic particle time-domain signal; and
    S400, performing a model reconstruction based on the high-quality magnetic particle time-domain signal to acquire a high-precision model, wherein
    the DNN fused with the self-attention mechanism comprises a feature extraction module, a joint denoising module, a time-frequency domain denoising module, and a feature reconstruction module;
    the feature extraction module is configured to transmit an extracted primary feature map to the joint denoising module and the time-frequency domain denoising module;
    the joint denoising module is configured to extract a global spatial feature based on the primary feature map and acquire a jointly denoised feature map;
    the time-frequency domain denoising module is configured to extract local features from a time-domain dimension and a frequency-domain dimension of the primary feature map, and fuse the local features of the time-frequency spectrum into a time-frequency domain-denoised feature map;
    the jointly denoised feature map and the time-frequency domain-denoised feature map are connected to generate feature connection information; and
    the feature reconstruction module is configured to perform a feature reconstruction based on the feature connection information so as to acquire a noise-free time-frequency spectrum.

2. The method for reconstructing the magnetic particle distribution model based on the time-frequency spectrum enhancement according to claim 1, wherein the feature extraction module specifically comprises:
    a feature extraction module input end, a multi-size feature analysis unit, a first feature concatenation unit, a first feature fusion convolutional layer, and a feature extraction module output end, wherein
    the multi-size feature analysis unit comprises a first branch, a second branch, and a third branch that are connected in parallel by the feature extraction module input end;
    the first branch comprises a convolutional layer with 16 1×1 convolutional kernels;
    the second branch comprises two sequentially connected convolutional layers, namely a convolutional layer with 16 1×1 convolutional kernels and a convolutional layer with 32 3×3 convolutional kernels;
    the third branch comprises three sequentially connected convolutional layers, namely a convolutional layer with 16 1×1 convolutional kernels, a convolutional layer with 32 3×3 convolutional kernels, and a convolutional layer with 64 3×3 convolutional kernels;
    an output of the first branch, an output of the second branch, and an output of the third branch are merged at an input of the first feature concatenation unit, and an output of the first feature concatenation unit is connected to the first feature fusion convolutional layer; and
    the feature extraction module input end is in a residual connection to the first feature fusion convolutional layer; and an input of the feature extraction module input end and an output of the first feature fusion convolutional layer are added together for output.

3. The method for reconstructing the magnetic particle distribution model based on the time-frequency spectrum enhancement according to claim 1, wherein the joint denoising module specifically comprises: a joint denoising module input end, a spatial attention block, a self-attention unit, a second feature fusion convolutional layer, a third feature fusion convolutional layer, and a joint denoising module output end that are sequentially connected;

the spatial attention block comprises a spatial attention block input end connected to a channel average pooling layer and a channel max pooling layer; an output of the channel average pooling layer and an output of the channel max pooling layer are jointly connected to an input of a second feature concatenation unit; an output of the second feature concatenation unit is sequentially connected to a convolutional layer with one 3×3 convolutional kernel and a Sigmoid layer; the joint denoising module input end is connected to the Sigmoid layer; and an input of the joint denoising module input end and an output of the Sigmoid layer are subjected to a matrix multiplication for output; and the self-attention unit comprises two parallel k×k self-attention blocks with different receptive fields, wherein k=3.5; and outputs of the two k×k self-attention blocks are added together, are then sequentially connected to the second feature fusion convolutional layer and the third feature fusion convolutional layer, and are connected to the joint denoising module output end.

4. The method for reconstructing the magnetic particle distribution model based on the time-frequency spectrum enhancement according to claim 3, wherein the self-attention blocks each comprise the following components that are sequentially connected: a self-attention block input end, a first k×k convolutional layer, a first Reshape layer, a first addition unit, six self-attention layers, a second Reshape layer, a second k×k convolutional layer, a second addition unit, a third k×k convolutional layer, a first rectified linear unit (ReLU) layer, and a self-attention block output end;

an output of the first Reshape layer is connected in parallel to the first addition unit and a position encoding layer;

an output of the position encoding layer is connected to the first addition unit; and the self-attention block input end is in a residual connection to the second addition unit.

5. The method for reconstructing the magnetic particle distribution model based on the time-frequency spectrum enhancement according to claim 4, wherein the self-attention layers each comprise the following components that are sequentially connected: a self-attention layer input end, a multi-head attention layer, a third addition unit, a first layer-normalization layer, a feedforward network, a fourth addition unit, a second layer-normalization layer, and a self-attention layer output end;

the self-attention layer input end is in a residual connection to the third addition unit; the feedforward network comprises a first fully connected layer, a Gaussian error linear unit (GeLU) layer, and a second fully connected layer that are sequentially connected;

the multi-head attention layer comprises the following components that are sequentially connected: a multi-head attention layer input end, 8 parallel dot-product attention blocks, a feature concatenation layer, a third fully connected layer, and a multi-head attention layer output end;

the dot-product attention block comprises a first dot-product fully connected layer, a second dot-product fully connected layer, and a third dot-product fully connected layer that are parallel with each other;

an output of the first dot-product fully connected layer and an output of the second dot-product fully connected layer are jointly connected to a matrix multiplication unit, and are sequentially connected to a normalization layer and a softmax layer; and an output of the softmax layer and the third dot-product fully connected layer are jointly connected to the matrix multiplication unit and a dot-product attention block output end.

6. The method for reconstructing the magnetic particle distribution model based on the time-frequency spectrum enhancement according to claim 1, wherein the time-frequency domain denoising module comprises a time-frequency domain denoising module input end, a time-domain denoising branch, a frequency-domain denoising branch that are sequentially connected; and the time-domain denoising branch and the frequency-domain denoising branch are parallel with each other, and are merged to form a fifth feature fusion convolutional layer and a time-frequency domain denoising module output end;

the time-domain denoising branch comprises the following components that are sequentially connected: a time-domain denoising branch input end, 10 consecutive time-domain attention blocks, and a convolutional layer with 16 1×1 convolutional kernels;

the time-domain attention block comprises a time-domain attention block input end, a first convolutional layer with 32 1×$k_1$ convolutional kernels, a second ReLU layer, a second convolutional layer with 32 1×$k_1$ convolutional kernels, a global average pooling layer, a Sigmoid layer, a multiplication unit, a fourth addition unit, and a time-domain attention block output end; an input of the global average pooling layer is connected to the multiplication unit; and the time-domain denoising branch input end is in a residual connection to the fourth addition unit; and the frequency-domain denoising branch is configured to replace the first convolutional layer with 32 1×$k_1$ convolutional kernels and the second convolutional layer with 32 1×$k_1$ convolutional kernels in the time-domain attention block respectively with a first convolutional layer with 32 $k_1$×1 convolutional kernels and a second convolutional layer with 32 $k_1$×1 convolutional kernels, replace the time-domain denoising branch input end and a time-domain denoising branch output end respectively with a frequency-domain denoising branch input end and a frequency-domain denoising branch output end, and remain a rest part the same as the time-domain denoising branch.

7. The method for reconstructing the magnetic particle distribution model based on the time-frequency spectrum enhancement according to claim 1, wherein the feature reconstruction module comprises a feature reconstruction module input end, 6 consecutive groups of densely connected layer-dense addition unit, and a feature reconstruction module output end; and the densely connected layers each comprise a densely connected layer input end connected to all dense addition units after the densely connected layers in a skip layer connection manner and sequentially connected to a sixth feature fusion convolutional layer, a seventh feature fusion convolutional layer, and the feature reconstruction module output end; and the densely connected layers each specifically further comprise the following components that are sequentially connected to the densely connected layer input end: a first batch-normalization layer, a third ReLU layer, a convolutional layer with 36 1×1 convolutional kernels, a second batch-normalization layer, a fourth ReLU layer, a convolutional layer with 12 3×3 convolutional kernels, and a densely connected layer output end.

8. The method for reconstructing the magnetic particle distribution model based on the time-frequency spectrum enhancement according to claim 1, wherein a training method of the DNN fused with the self-attention mechanism comprises:

A100, acquiring training data with a ground-truth label as to-be-processed data, wherein the to-be-processed data is specifically acquired as follows:

acquiring a simulated dot image, and extracting a one-dimensional time-domain signal of the simulated dot image;

superposing noise on the one-dimensional time-domain signal of the simulated dot image to acquire a noisy one-dimensional time-domain signal;

performing short-time Fourier transform on the one-dimensional time-domain signal of the simulated dot image and the noisy one-dimensional time-domain signal to acquire a simulated two-dimensional time-frequency spectrum and a noisy simulated two-dimensional time-frequency spectrum; and taking the noisy simulated two-dimensional time-frequency spectrum as the training data and the simulated two-dimensional time-frequency spectrum as a ground-truth label for the training data;

A200, inputting the to-be-processed data into the DNN fused with the self-attention mechanism;

A300, extracting, by the feature extraction module, feature maps of different sizes based on the to-be-processed data; concatenating the feature maps of different sizes; processing, by a convolutional layer, the feature maps of different sizes; and adding the feature maps of different sizes together with the to-be-processed data, so as to acquire the primary feature map;

A400, acquiring, by the joint denoising module, a channel max pooling attention feature and a channel average pooling attention feature based on the primary feature map; introducing learnable position information encoding; acquiring a global feature through multi-head attention; and acquiring the jointly denoised feature map; and acquiring, by the time-frequency domain denoising module, a time-domain feature map and a frequency-domain feature map based on the primary feature map; and adding the time-domain feature map and the frequency-domain feature map together to acquire the time-frequency domain-denoised feature map;

A500, adding the jointly denoised feature map and the time-frequency domain-denoised feature map together to form a combined feature map; and performing, by the feature reconstruction module, the feature reconstruction on the combined feature map through multiple densely connected layers and convolutional layers to generate the denoised magnetic particle time-frequency spectrum;

A600, calculating, based on the denoised magnetic particle time-frequency spectrum, a training loss:

$$L_{all}=0.5*L_{real}+L_{imag}$$

wherein, $L_{real}$ denotes a real part error, calculated by an average absolute error; and $L_{imag}$ denotes an imaginary part error, calculated by an average square error; and A700, repeating steps A200 to A600 until the training loss is below a preset threshold or reaches a preset number of iterations, so as to acquire the trained DNN fused with the self-attention mechanism; and performing the inverse Fourier transform on the generated denoised magnetic particle time-frequency spectrum to acquire the high-quality magnetic particle time-domain signal.

9. The method for reconstructing the magnetic particle distribution model based on the time-frequency spectrum enhancement according to claim 8, wherein the operation of superposing the noise on the one-dimensional time-domain signal of the simulated dot image to acquire the noisy one-dimensional time-domain signal specifically comprises:

superposing a harmonic interference and a Gaussian noise on the one-dimensional time-domain signal of the simulated dot image:

$$u_n(t)=u(t)+u_G(t)+u_h(t)$$

wherein, u(t) denotes the one-dimensional time-domain signal of the simulated dot image; $u_G(t)$ denotes the Gaussian noise; $u_h(t)$ denotes the harmonic interference; and $u_n(t)$ denotes the noisy one-dimensional time-domain signal;

$$u_h(t) = \sum_{n=1}^{6} A_n \sin(2\pi f_n t + \theta_n)$$

n denotes an n-th harmonic; $f_n$ denotes a harmonic frequency; $\theta_n$ denotes a random phase that is uniformly distributed in $[0,2\pi]$; and $A_n$ denotes an amplitude of an additional harmonic;

the amplitude of the additional harmonic is calculated according to a signal interference ratio equation:

$$SIR = 20\log_{10}\left(\frac{\max_{f_n}|U_n(f_n)|}{A_n}\right)$$

wherein, SIR denotes a set noise level; and $U_n(*)$ denotes a bandwidth of the n-th harmonic of the one-dimensional time-domain signal of the simulated dot image; the Gaussian noise $u_G(t)$ is calculated as follows:

$$SNR = 20\log_{10}\left(\frac{\max_{t}|u(t)|}{\sigma}\right)$$

wherein, SNR denotes a signal-to-noise ratio; $\sigma$ denotes a standard deviation of noise; and u(t) denotes the one-dimensional time-domain signal of the simulated dot image.

10. A system for reconstructing a magnetic particle distribution model based on a time-frequency spectrum enhancement, comprising:

a one-dimensional time-domain signal acquisition module, configured to scan a scan target by an MPI device so as to acquire a one-dimensional time-domain signal of the scan target;

a two-dimensional time-frequency spectrum acquisition module, configured to perform short-time Fourier transform on the one-dimensional time-domain signal of the scan target to acquire a two-dimensional time-frequency spectrum;

a frequency-spectrum denoising module, configured to acquire, by a trained DNN fused with a self-attention mechanism, a denoised magnetic particle time-frequency spectrum based on the two-dimensional time-frequency spectrum; and perform inverse Fourier transform to acquire a high-quality magnetic particle time-domain signal; and a model reconstruction module, configured to perform a model reconstruction based on the high-quality magnetic particle time-domain signal so as to acquire a high-precision model; and the DNN fused with the self-attention mechanism comprises a feature extraction module, a joint denoising module, a time-frequency domain denoising module, and a feature reconstruction module;

the feature extraction module is configured to transmit an extracted primary feature map to the joint denoising module and the time-frequency domain denoising module;

the joint denoising module is configured to extract a global spatial feature based on the primary feature map and acquire a jointly denoised feature map;

the time-frequency domain denoising module is configured to extract local features from a time-domain dimension and a frequency-domain dimension of the primary feature map, and fuse the local features of the time-frequency spectrum into a time-frequency domain-denoised feature map;

the jointly denoised feature map and the time-frequency domain-denoised feature map are connected to generate feature connection information; and the feature reconstruction module is configured to perform a feature reconstruction based on the feature connection information so as to acquire a noise-free time-frequency spectrum.

* * * * *